United States Patent
Kuo et al.

(10) Patent No.: US 6,838,019 B2
(45) Date of Patent: Jan. 4, 2005

(54) PHOSPHORESCENT MATERIAL AND ELECTROLUMINESCENT DEVICE USING THEREOF

(75) Inventors: Chao-Nan Kuo, Hsinchu Industrial Park (TW); Mei-Jung Hu, Hsinchu Industrial Park (TW); Sung-Kuei Chiang, Hsinchu Industrial Park (TW)

(73) Assignee: Ritek Corporation, Hsinchu (TW)

( * ) Notice: Subject to any disclaimer, the term of this patent is extended or adjusted under 35 U.S.C. 154(b) by 19 days.

(21) Appl. No.: 10/212,279

(22) Filed: Aug. 1, 2002

(65) Prior Publication Data

US 2003/0102800 A1 Jun. 5, 2003

(30) Foreign Application Priority Data

Aug. 9, 2001 (TW) ........................................ 90119460 A

(51) Int. Cl.⁷ .......................... C09K 11/02; C09K 11/06
(52) U.S. Cl. ............................ 252/301.35; 252/301.14; 252/301.15
(58) Field of Search ....................... 252/301.35, 301.19, 252/301.15

(56) References Cited

U.S. PATENT DOCUMENTS 5,158,703 A * 10/1992 Takuma et al.

OTHER PUBLICATIONS

Golodkooa et al, CA 104: 110 945, 1986.*
Powers et al, Ca 115: 70672, 1991.*
Iwase et al, CA 119: 58174, 1993.*
Maha Lak Shmi et al, CA 128: 200046, 1998.*

* cited by examiner

Primary Examiner—Deborah C. Lambkin
(74) Attorney, Agent, or Firm—J.C. Patents

(57) ABSTRACT

A phosphorescent light emitting material, the material is a complex compound comprises a beta-diketonate ligand, a sulfoxide ligand and a triple charge rare earth group metal ion, the phosphorescent light emitting material has a following structure:

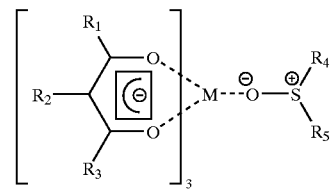

wherein M is a triple charge rare earth group metal ion, $R_2$ is hydrogen, $R_1$ and $R_3$ are selected from the group consisting of, hydrogen, $C_1$ to $C_8$ straight chain alkyl groups, $C_3$ to $C_8$ branch chain alkyl groups, heterocyclic groups and $C_6$ to $C_{14}$ aryl groups, and $R_4$ and $R_5$ are selected from the group consisting of substituted alkyl group, an unsubstituted alkyl group, an aryl group and a heterocyclic group.

33 Claims, No Drawings

PHOSPHORESCENT MATERIAL AND ELECTROLUMINESCENT DEVICE USING THEREOF

CROSS-REFERENCE TO RELATED APPLICATION

This application claims the priority benefit of Taiwan application serial no. 90119460, filed Aug. 9, 2001.

BACKGROUND OF THE INVENTION

1. Field of the Invention

The present invention relates to an organic electroluminescent material. More particularly, the present invention relates to a phosphorescent material.

2. Description of Related Art

An organic electroluminescent device is a semiconductor device in which electrical power is converted to optical power with a high conversion rate. Since the characteristics of a majority of the organic electroluminescent devices are similar to those of a photodiode, the organic electroluminescent device is also known as an organic light emitting diode. An organic light emitting diode is commonly used as an indicator, a display panel and an optical pick-up light-emitting device. Further, the organic light emitting diode comprises special characteristics, such as, low operation voltage of less than 10 volts, quantum efficiency greater than 1%, simple processing, low cost, high response rate, broad temperature range and full color, the display characteristics demanded by the multi-media era can be accommodated. The research on organic light emitting diode thus becomes a very popular topic in recent years.

The basic structure of an organic light emitting diode (OLED) includes a glass substrate, a metal electrode, an indium tin oxide electrode and an organic elecctroluminescent (OEL) layer. The optical emission mechanism behind an organic light emitting diode is based upon the radiative recombination of a trapped charge. Specifically, an OLED comprises a metal electrode as the anode and an indium tin oxide (ITO) as the cathode. As a forward bias is applied to the electrodes, electrons and holes from the metal electrode and the ITO electrode, respectively, are injected into a luminescent layer. When the injected holes and the injected electrons are recombined, a photon is formed by radiative recombination and a light emission effect is resulted. Since the electron transmission speed is faster than the hole transmission speed, a hole injection layer (HIL) and a hole transport layer (HTL) can form between the ITO electrode and the luminescent layer and an electron injection layer (EIL) and electron transport layer (ETL) are formed between the luminescent layer and the metal electrode to provide an electron and hole transmission balance parameter of about 1. An equilibrium between electron and hole injection/transport is thereby maintained.

In an organic light emitting device, the organic light emitting layer is mainly selected from two types of material: a low molecular dye or a high molecular polymer. The fundamental principle of the two types of material, however, is the same. The light emission mechanism of an OLED material is derived from the fluorescent generated mechanism of the OLED material. When a molecule absorbs an appropriate amount of energy, the electrons at the ground state are excited to the excited state. The excited electrons are known as excitons. The excitons then drop back to the ground state and release energy in various forms (light or heat). If light is emitted during the transition from an excited state to a ground state, fluorescence or phosphorescence is generated. A stable molecule comprises an even number of electrons. In other words, when the electrons are paired and are spin in opposite directions, the energy of the molecule is at the ground state. As the molecule absorbs an appropriate amount of energy, the electrons in the $S_0$ state is excited to a higher singlet excited state $S_1$, or through inter system crossing, (ISC) to the excited triplet state ($T_1$). For a fluorescent molecule, electrons at the singlet excited state radiatively drops to any vibration energy level to emit fluorescence. Phosphorescence is emitted as electrons are dropped from the excited triplet state to the ground state. The light emission efficiency of phosphorescent light is better than that of the fluorescent light.

A typical phosphorescent light emitting material used in the above OLED layer is β-diketonate triple charge metal complex compound ($ML1_3$), wherein M is a triple charge metal ion ($M^{3+}$), and the ligand L1 is β-diketonate. The solubility of this type of complex compound is poor; therefore, it is difficult to process $M^{3+}$β-diketonate to form thin film. A conventional approach to improve the solubility of the $M^{3+}$β-diketonate complex compound is to incorporate another ligand to this complex compound as described in WO00/32718. Example of such includes the Tb(TMHD)$_3$—OPNP complex compound (III), (Tris(2,2,6,6-tetramethyl-3,5-heptanedionato)Terbium (III) diphenyl phosphonimide tris-phenyl phosphorane). The structure of Tb(TMDH)$_3$—OPNP (I) is indicated below:

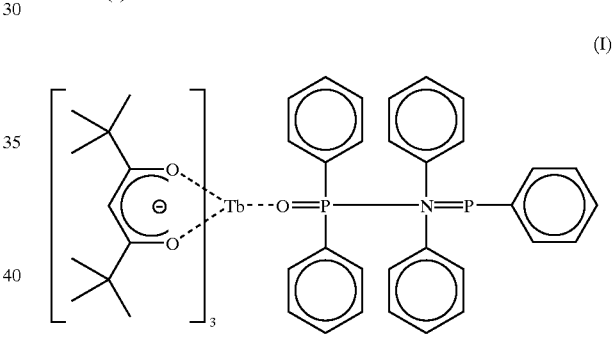

(I)

Using the above Tb(TMHD)$_3$—OPNP complex compound (III) as the luminescent layer for the organic light emitting diode, a thin film of Tb(TMHD)$_3$—OPNP is deposited by evaporation. The melting point of the Tb(TMHD)$_3$—OPNP complex compound (III) is high (246 degree Celsius to about 248 degrees Celsius). Therefore, forming a thin film by evaporation requires conducting at a higher temperature. A higher manufacturing cost is thereby resulted.

SUMMARY OF THE INVENTION

Accordingly, the present invention provides a phosphorescent material, wherein the melting point of this material is lower. Deposition by evaporation is thereby easier to lower the manufacturing cost.

The present invention further provides a phosphorescent material, wherein the solubility of this material is improved. The material of the present invention can dissolve in an organic solvent. Therefore, this material provides a desirable workability, and can be formed into a thin film by the spin coating method.

In accordance to the present invention, a phosphorescent light emitting material is provided, wherein the abbreviated formula for the phosphorescent light emitting material is $M(L1)_3L2$, which includes triple charge earth group metal ion (M) combined with three diketonate ligands (L1) and sulfoxide ligands (L2).

The diketonate ligands can be alpha-diketonate, beta-diketonate or gamma-diketonate.

If the diketonate ligand (L1) is a beta-diketonate ligand, the structure of this type of phosphorescent light emitting material (II) is:

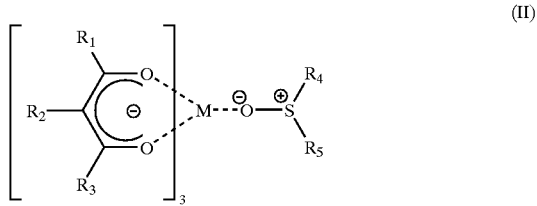

In the above structure, M is a rare earth group metal ion, for example, La(III), Sm(III), Eu(III), Tb(III), Dy(III), Yb(III), Lu(III) or Gd(III), etc.

The $R_1$ and $R_3$ in beta-diketonate are, for example, hydrogen, substituted alkyl group, unsubstitued alkyl group, aryl group or heterocyclic group, wherein the alkyl group includes $C_1-C_8$ straight chain or branch chain alkyl, such as, methyl, ethyl, propyl, isopropyl, butyl, pentyl, etc. The aryl group includes $C_6-C_{14}$ aryl, such as, phenyl, tolyl, xylyl, ethylbenzene, etc. The heterocyclic group includes, pyridyl, imidazolyl, furyl or thienyl group. The alkyl group, aryl group or heterocyclic group in $R_1$ and $R_3$ can be substituted with halide, cyanide or alkoxy, for example, chloride, methoxy, etc., wherein $R_1$ and $R_3$ can form with a same functional group or different functional groups, and $R_2$ is hydrogen.

The beta-diketonate ligand includes, acetyl acetone, tri(2,2,6,6-tetramethyl-3,5-heptanedione, dibenzoyl methane, dinathphoyl methane, benzoyl acetione, thenoyl trifluoroacetone, 1,3-di(2-furyl)-1,3-propanedione, nathphoyl trifluoroacetone, etc.

The gamma-diketonate ligand includes 2(4'-methoxy benzoyl) benzoate.

The $R_4$ and $R_5$ groups in the sulfoxide ligand (L2) are, for example, an alkyl group such as a substituted alkyl group or an unsubstituted alkyl group, a heterocyclic group or an aryl group. The alkyl group includes $C_1-C_8$ straight chain or branch chain alkyl, such as, methyl, ethyl, propyl, isopropyl, butyl, pentyl, etc. The aryl group includes $C_6-C_{14}$ aryl, such as, phenyl, tolyl, xylyl, ethylbenzene, etc. The alkyl group or the aryl group in $R_4$, $R_5$ can be substituted with halide, cyanide or alkoxy, such as chloride or methoxy, etc. Further, $R_4$ and $R_5$ can form with a same functional group or different functional groups.

The sulfoxide ligand includes dimethyl sulfoxide (DMSO), diethyl sulfoxide (DESO), dipropyl sulfoxide (DPrSO), dibutyl sulfoxide (DBuSO), dipentyl sulfoxide (DPeSO), dihexyl sulfoxide (DHSO), diphenylsulfoxide (DPSO), methyl ethyl sulfoxide (MPSO), methyl propyl sulfoxide (MPrSO), methyl butyl sulfoxide (MBSO), ethyl propyl sulfoxide (EPrSO), ethyl butyl sulfoxide (EBSO), propyl butyl sulfoxide (PrBSO), methyl phenyl sulfoxide (MPSO), ethyl phenyl sulfoxide (EPSO), propyl phenyl sulfoxide (PrPSO), butyl phenyl sulfoxide (BPSO), methyl tolyl sulfoxide (MTSO), ethyl tolyl sulfoxide (ETSO), propyl tolyl sulfoxide (PrTSO), butyl tolyl sulfoxide (BTSO), methyl xylyl sulfoxide (MXSO), ethyl xylyl sulfoxide (EXSO), propyl xylyl sulfoxide (PrXSO) or butyl xylyl sulfoxide (BXSO). The sulfoxide includes $C_1-C_8$ alkyl or $C_6-C_{14}$ aryl, symmetrical or asymmetrical sulfoxide.

The present invention provides an incorporation of sulfoxide ligand to a diketonate triple charge rare earth group metal ion complex compound to form a diketonate sulfoxide triple charge rare earth group metal ion complex compound, wherein the solubility of the complex compound is increased while the melting point of the complex compound is decreased to enhance the workability of the compound.

It is to be understood that both the foregoing general description and the following detailed description are exemplary, and are intended to provide further explanation of the invention as claimed.

DESCRIPTION OF THE EMBODIMENTS

The following embodiment details the phosphorescent light emitting material of the present invention.

The diketone sulfoxide triple charge rare earth group metal ions complex compound is abbreviated as $M(L1)_3L2$, wherein M represents the triple charge rare earth group metal ion, L1 represents the diketonate ligand and L2 represents the sulfoxide ligand.

The diketonate ligand (L1) can be an alpha-diketonate ligand, a beta-diketonate ligand or a gamma-diketonate ligand.

If the diketonate ligand (L1) is beta-diketonate, the structure of the complex compound (II) is

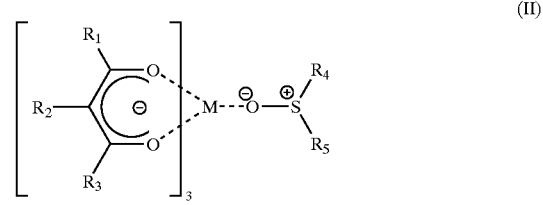

The triple charge rare earth metal ions (M) includes, for example, La(III), Sm(III), Eu(III), Tb(III), Dy(III), Yb(III), Lu(III), Gd(III), etc.

The $R_1$ and $R_3$ groups in beta-diketonate are, for example, hydrogen, a substituted alkyl group, an unsubstituted alkyl group, an aryl group or a heterocyclic group. The alkyl group is $C_1-C_3$ straight chain or branch chain alkyl, such as, methyl, ethyl, propyl, isopropyl, butyl, pentyl, etc. The aryl group is $C_6-C_{14}$ aryl, such as, phenyl, tolyl, xylyl, ethylbenzene, etc. The heterocyclic group is, for example, pyridyl, imidazoly, furyl or thienyl group. The alkyl group, the aryl group or the heterocyclic group in $R_1$ and $R_3$ can be replaced substituted with halide, cyanide or alkoxy, for example, chloride, methoxy, etc., wherein $R_1$ and $R_3$ can form with a same functional group or different functional groups, and $R_2$ is hydrogen.

The $R_4$ and $R_5$ in the sulfoxide ligand (L2) are, for example, an alkyl group such as a substituted alkyl group or an unsutstituted alkyl group, a heterocyclic group, or an aryl group. The alkyl group includes $C_1-C_8$ straight chain or branch chain alkyl, such as, methyl, ethyl, propyl, isopropyl, butyl, pentyl, etc. The aryl group includes $C_6-C_{14}$ aryl, such as, phenyl, tolyl, xylyl, ethylbenzene, etc. The alkyl group or aryl group in $R_4$ and $R_5$ can be substituted with halide, cyanide or alkoxy, such as chloride or methoxy, etc. Further, $R_4$ and $R_5$ can form with a same functional group or different functional groups.

Using a beta-diketonate sulfoxide triple charge rare earth metal ion complex compound as an example, the phosphorescence light emitting material of the present invention is formed by coordination reaction with equal moles of sulfoxide ligands and beta-diketonate triple charge rare earth group metal ion complex compound. Sulfoxide is first dissolved in a dichloromethane/acetonitrile solvent, followed by incorporating beta-diketonate triple charge rare earth metal group ion complex compound. Nitrogen gas is also introduced into the reactor. The solution is subjected to thermal reflux for 2 hours and is then cooled to room temperature. The solvent is then extracted until the final volume of the solution is half of the original volume when sediment is formed. After filtering the sediment, the filtered sediment is re-crystallized to obtain the beta-diketonate sulfoxide triple charge rare earth group metal ion complex compound.

The above beta-diketonate triple charge rare earth group metal ion complex compound includes tri(acetylacetonato) Terbium (III) (Tb(AcA)$_3$), tri(2,2,6,6)-tetramethyl-3,5-heptanedionate) Terbium (III) (Tb(TMHD)$_3$), tri(dibenzoylmethane) Terbium (III) Tb(DBM)$_3$), tri(dinathphoylmethane) Terbium (III) (Tb(DNM)$_3$), tri(benzoylacetone) Terbium (III) (Tb(BAc)$_3$), tri(thenoyltrifluoroacetonato)Terbium (III) (Tb(TTA)$_3$), tri(1,3-di(2-furyl)-1,3-propanedione) Terbium(III) (Tb(DFP)$_3$), tri(nathphoyltrifluoroacetonate) Terium(III) (Tb(NTA)$_3$), tri(acetylacetonato) Europium (III) (Eu(AcA)$_3$), tri(2,2,6,6-tetramethyl-3,5-heptanedionate)Europium (III) (Eu(TMHD)$_3$), tri(dibenzoylmethane Europium (III) (Tb(DBM)$_3$), tri(dinathphoylmethane) Europium (III) (Eu(DNM)$_3$), tri(benzoylacetone) Europium (III) (Eu(BAc)$_3$), tri(thenoyltrifluoroacetonato) Europium (III) (Eu(TTA)$_3$), tri(1,3-di(2-furyl)-1,3-propanedione) Europium (III (Eu(DFP)$_3$), tri(nathphoyltrifluoroacetonato) Europium (III) (Eu(NTA)$_3$), or La (III), Sm(III), Dy(III), Yb(III), Lu(III), Gd(III).

The aforementioned sulfoxide ligand includes dimethyl sulfoxide (DMSO), diethyl sulfoxide (DESO), dipropyl sulfoxide (DPrSO), dibutyl sulfoxide (DBuSO), dipentyl sulfoxide (DPeSO), dihexyl sulfoxide (DHSO), diphenylsulfoxide (DPSO), methyl ethyl sulfoxide (MPSO), methyl ethyl sulfoxide (MPSO), methyl propyl sulfoxide (MPrSO), (methyl butyl sulfoxide (MBSO), ethyl propyl sulfoxide (EPrSO), ethyl butyl sulfoxide (EBSO), propyl butyl sulfoxide (PrBSO), methyl phenyl sulfoxide (MPSO), ethyl phenyl sulfoxide (EPSO), propyl phenyl sulfoxide (PrPSO), butyl phenyl sulfoxide (BPSO), methyl totyl sulfoxide (MTSO), ethyl tolyl sulfoxide (ETSO), propyl tolyl sulfoxide (PrTSO), butyl tolyl sulfoxide (BTSO), methyl xylyl sulfoxide (MXSO), propyl xylyl sulfoxide (PrXSO), butyl xylyl sulfoxide (BXSO). The sulfoxide includes $C_1$–$C_8$ alkyl or $C_6$–$C_{14}$ aryl, symmetrical or asymmetrical sulfoxide.

To further detail the present invention, three embodiments of the beta-diketone sulfoxide triple charge rare earth metal ioncomplex compound are discussed. In the first embodiment, (tri(2,2,6,6-tetramethyl-3,5-heptanedionate) Tb(III) dimethyl sulfoxide, Tb(TMHD)$_3$—DMSO) is discussed. In the second embodiment, (tri(2,2,6,6-tetramethyl-3,5-heptanedionate) Tb(III) methyl phenyl sulfoxide, Tb(TMHD)$_3$—MPSO) is discussed. In the third embodiment, tri(2,2,6,6-tetramethyl-3,5-heptanedionate) Tb(III) diphenyl sulfoxide, Tb(TMHD)$_3$—DPSO is discussed. Further, (tris(2,2,6,6-tetramethyl-3,5-heptanedionato) Terbium(III), Tb(TMHD)$_3$) is used in Comparative Test 1 while (Tris(2,2,6,6-tetramethyl-3,5-heptanedionato) Terbium (III) diphenyl phosphonimide tris-phenyl phosphorane, Tb(TMHD)$_3$—OPNP) is used in Comparative Test 2.

1.0 mmole of dimethyl sulfoxide is dissolved in dichloromethane/acetonitrile solution, wherein the mole ratio for dichloromethane to acetonitrile is 1:1. Thereafter, the dichloromethane/acetonitrile solution that comprises the dimethyl sulfoxide is placed in a reactor. 1.0 mmole of (tri(2,2,6,6-tetramethyl-3,5-heptanedionate) Tb(III), Tb(TMHD)$_3$ is also placed in the reactor, and a nitrogen gas is introduced into the reactor. The solution is subjected to thermal reflux for 2 hours and is then cooled to room temperature. Thereafter, the solvent is extracted with a rotary vacuum evaporator until the final volume of the solution is half of the original volume and when sediment is formed. After filtering the sediment, the filtered sediment is re-crystallized with methylcyclohexane to obtain the Tb(TMHD)$_3$—DMSO) complex compound.

1.0 mmole of methyl phenyl sulfoxide is dissolved in dichloromethane/acetonitrile solution, wherein the mole ratio for the dichloromethane/acetonitrile solution is 1:1. Thereafter, the dichloromethane/acetonitrile solution that comprises the methyl phenyl sulfoxide is placed in a reactor. 1.0 mmole of tri(2,2,6,6-tetramethyl-3,5-heptanedionate Tb(III) (Tb(TMHD)$_3$) is also placed in the reactor, and a nitrogen gas is introduced into the reactor. The solution is subjected to thermal reflux for 2 hours and is then cooled to room temperature. The solvent is extracted with a rotary vacuum evaporator until the final volume of the solution is half of the final volume and when sediment is formed. After filtering the sediment, the filtered sediment is re-crystallized to obtain a Tb(TMHD)$_3$—MPSO complex compound.

1.0 mmole of diphenyl sulfoxide is dissolved in dichloromethane/acetonitrile solution, wherein the mole ratio for the dichloromethane/acetonitrile solution is 1:1. Thereafter, the dichloromethane/acetonitrile solution that comprises the diphenyl sulfoxide sulfoxide is placed in a reactor. 1.0 mmole of tri(2,2,6,6-tetramethyl-3,5-heptanedionate Tb(III) (Tb(TMHD)$_3$) is also placed in the reactor, and a nitrogen gas is introduced into the reactor. The solution is subjected to thermal reflux for 2 hours and is then cooled to room temperature. The solvent is extracted with a rotary vacuum evaporator until the final volume of the solution is half of the original volume and when sediment is formed. After filtering the sediment, the filtered sediment is re-crystallized to obtain a Tb(TMHD)$_3$—DPSO complex compound.

Comparative Test 1

<Tb(TMHD)$_3$ Complex Compound>

Purchase from Strem Chemistry Company. Purity: 99%. Solubility: 155° C. to 156°C.

Comparative Test 2

<Formation of Tb(TMHD)$_3$—OPNP Compound>

1.0 mmole of diphenyl phosphonimide tris-pheny phosphorane (OPNP) is dissolved in a dichloromethane solution. The dichlormethane solution that comprises OPNP is then placed in a reactor. 1.0 mmole of tri(2,2,6,6-tetramethyl-3,5-heptanedionate) Tb(III), (Tb(TMHD)$_3$) is also placed in the reactor, and a nitrogen gas is introduced into the reactor. The solution is subjected to thermal reflux for 2 hours and is then cooled to room temperature. The solvent is extracted with a rotary vacuum evaporator until the final volume of the solution is of the original volume and when sediment is formed. After filtering the sediment, the filtered sediment is re-crystallized to obtain a Tb(TMHD)$_3$—OPNP complex compound.

Solubility Test 1 mg of Tb(TMHD)$_3$—DMSO, Tb(TMHD)$_3$—MPSO, Tb(TMHD)$_3$—DPSO, Tb(TMHD)$_3$, Tb(TMHD)$_3$—OPNP are each dissolved under room temperature (20 degrees Celsius) in the following organic solvent: dichlormethane, acetonitrile, toluene, ethyl acetate, hexane, methyl cyclohexane methanol, methy ethyl ketone ether. Results of the solubility test is summarized in Table 1.

TABLE 1

|  | Tb(TMHD)$_3$-DMSO | Tb(TMHD)$_3$-MPSO | Tb(TMHD)$_3$-DPSO | Tb(TMHD)$_3$ | Tb(TMHD)$_3$-OPNP |
|---|---|---|---|---|---|
| Dichloromethane | ⊙ | ⊙ | ⊙ | ○ | ⊙ |
| Acetonitrile | ○ | ○ | ○ | X | ○ |
| Toluene | ⊙ | ⊙ | ⊙ | ○ | ⊙ |
| Ethylacetate | ⊙ | ⊙ | ⊙ | X | ⊙ |
| Hexane | ⊙ | ⊙ | ⊙ | X | ○ |
| Methylcyclohexane | ⊙ | ⊙ | ⊙ | X | ○ |
| Methanol | ⊙ | ⊙ | ⊙ | X | ○ |
| Methyl ethyl ketone | ⊙ | ⊙ | ⊙ | X | ⊙ |
| Ether | ⊙ | ⊙ | ⊙ | ○ | ⊙ |

X: not dissolved
○: partially dissolved
⊙: completely dissolved

<Solubility Test>

Differential Scanning Calorimetry (Mettler Toledo Differential Scanning Calorimeter (DSC-821)) is used to determine the melting points for Tb(TMHD)$_3$—DMSO, Tb(TMHD)$_3$—MPSO, Tb(TMHD)$_3$—DPSO, Tb(TMHD)$_3$, Tb(TMHD)$_3$—OPNP and the results are summarized in Table 2. The ascending and the descending temperature rates are 10° C./min.

Relative Quantum Efficiency Test

The quantum efficiencies of Tb(TMHD)$_3$—DMSO, Tb(TMHD)$_3$—MPSO, Tb(TMHD)$_3$—DPSO, Tb(TMHD)$_3$—OPNP are compared with that of the standard Tb(TMHD)$_3$.

An appropriate amount of Tb(TMHD)$_3$—DMSO, Tb(TMHD)$_3$—MPSO, TB(TNHD)$_3$—DPSO, Tb(TMHD)$_3$—OPNP is dissolved in a dichloromethane solvent to a form a diluted solution having an optical density of 0.5 for the UV-VIS absorption (Instrument used: Hitachi UV-Vis spectrophotometer 3010). The fluorescence of the various samples is compared with that of the standard (Instrument used: Hitachi fluorescence spectrophotometer F-4500) and the results are presented in terms relative quantum efficiencies calculated using the relative quantum efficiency formula:

$$(\Phi s/\Phi st) = (As/Ast) \times (ODst/ODs) \times (Qst/Qs) \times 100\%$$

Φs: fluorescence quantum efficiency of the sample
Φst: fluorescence quantum efficiency of the standard
As: area under the fluorescence spectrum line of the sample
Ast: area under the fluorescence spectrum line of the standard
ODs: degree of absorption of the sample under the maximum wavelength λmax of the UV-VIS spectrum
ODst: degree of absorption of the standard under the maximum wavelength λmax of the UV-VIS spectrum
Qs: number of photons provided to the sample by the fluorescence exciting light source
Qst: number of photons provided to the standard by the fluorescence exciting light source Under a same intensity of the light source, Qst/Qs is equal to 1 Therefore, under the same intensity of the light source and by obtaining the integrated area and the OD value of the UV-VIS spectrum, the relative quantum efficiency is determined. Table 2 summarizes the relative quantum efficiencies and the maximum wavelengths λ max of the UV-VIS spectrum for the different samples.

TABLE 2

|  | Melting Temperature (° C.) | UV λ max (nm) (CH$_2$Cl$_2$) | Emission Peak λ max | Relative Quantum Efficiency (%) |
|---|---|---|---|---|
| Tb(TMHD)$_3$-DMSO | 164.3 | 282.2 | 559 | 0.74 |
| Tb(TMHD)$_3$-MPSO | 91.0 | 283.2 | 556 | 0.93 |
| Tb(TMHD)$_3$-DPSO | 165.4 | 281.8 | 556 | 1.21 |
| Tb(TMHD)$_3$ | 156 | 273.4 | 556 | 1.00 |
| Tb(TMHD)$_3$-OPNP | 268 | 278.6 | 557 | 0.67 |

Based on the results summarized in Table 1, comparing Tb(TMHD)$_3$-DMSO, Tb(TMHD)$_3$-MPSO, Tb(TNHD)$_3$-DPSO, Tb(TMHD)$_3$-OPNP with Tb(TMHD)$_3$, the complex compounds formed according to the present invention can be dissolved in more types of solvent. Since these compounds have a higher solubility in the various organic solvents, they can be formed as thin film by a spin coating method.

The results in Table 2 indicate that the melting point of Tb(TMHD)$_3$—DMSO, Tb(TMHD)$_3$—MPSO and Tb(TNHD)$_3$—DPSO are lower than that of Tb(TMHD))$_3$—OPNP. Therefore during the deposition of a thin film by evaporation, a lower temperature is needed to reduce the cost.

Further, the quantum efficiencies for Tb(TMHD)$_3$—DMSO, Tb(TMHD)$_3$—MPSO, Tb(TNHD)$_3$—DPSO are higher than that for Tb(TMHD)$_3$—OPNP.

One aspect of present invention is the incorporation of sulfoxide to a diketonate triple charge rare earth metal ion complex compounds. The solubility of the compound in an organic solvent is increased and the melting point of the compound is decreased to increase the workability of the compound.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A phosphorescent light emitting material with an abbreviated chemical formula of M(L1)$_3$L2, wherein
   M is a triple charge rare earth group metal ion;
   L1 is a diketonate ligand; and
   L2 is a sulfoxide ligand;
   wherein the phosphorescent light emitting material is used for forming a thin film of an electroluminescent device.

2. The phosphorescent light emitting material of claim 1, wherein the triple charge rare earth metal ion is selected from the group consisting of La(III), Sm(III), Eu(III), Tb(III), Dy(III), Yb(III), Lu(III) and Gd(III).

3. The phosphorescent light emitting material of claim 1, wherein the diketonate ligand is selected from the group consisting of an alpha-diketonate ligand, a beta-diketonate ligand and a gamma-diketonate ligand.

4. The phosphorescent light emitting material of claim 3, wherein the beta-diketonate ligand has a following structure:

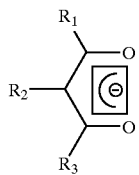

R$_2$ is hydrogen, R$_1$ and R$_3$ is are formed with a same functional group or different functional groups, and R$_1$ and R$_3$ is selected from the group consisting of hydrogen, an unsubstituted alkyl group, a substituted alkyl group, an aryl group and a heterocyclic group.

5. The phosphorescent light emitting material of claim 4, wherein the substituted alkyl group is selected from the group comprising of C$_1$ to C$_8$ straight chain alkyl groups and C$_3$ to C$_8$ branch chain alkyl groups.

6. The phosphorescent light emitting material of claim 4, wherein the substituted alkyl group is substituted with halide.

7. The phosphorescent light emitting material of claim 4, wherein the substituted alkyl group is substituted with cyanide.

8. The phosphorescent light emitting material of claim 4, wherein the substituted alkyl group is substituted with an alkoxyl group.

9. The phosphorescent light emitting material of claim 4, wherein the aryl group is selected from the group consisting of C$_6$ to C$_{14}$ aryl groups.

10. The phosphorescent light emitting material of claim 4, wherein the heterocyclic group includes a pyridyl group.

11. The phosphorescent light emitting material of claim 4, wherein the heterocyclic group includes an imidazolyl group.

12. The phosphorescent light emitting material of claim 4, wherein the heterocyclic group includes a furyl group.

13. The phosphorescent light emitting material of claim 4, wherein the heterocyclic group includes a thienyl group.

14. The phosphorescent light emitting material of claim 1, wherein the sulfoxide ligand has a following structure:

R$_4$ and R$_5$ are formed with a same functional group or different functional groups, and R$_4$ and R$_5$ are selected from the group consisting of, a substituted alkyl group, an unsubstituted alkyl group, an aryl group and a heterocyclic group.

15. The phosphorescent light emitting material of claim 14, wherein the alkyl group is selected from the group consisting of C$_1$ to C$_8$ straight chain alkyl groups and C$_3$ to C$_8$ branch chain alkyl groups.

16. The phosphorescent light emitting material of claim 14, wherein the aryl group is selected from the group consisting of C$_6$ to C$_{14}$ aryl groups.

17. The phosphorescent light emitting material of claim 4, wherein the beta-diketonate includes acetyl acetone.

18. The phosphorescent light emitting material of claim 4, wherein the beta-diketonate includes tri(2,2,6,6-tetramethyl-3,5-heptanedione).

19. The phosphorescent light emitting material of claim 4, wherein the beta-diketonate includes dibenzoyl methane.

20. The phosphorescent light emitting material of claim 4, wherein the beta-diketonate includes dinathphoyl methane.

21. The phosphorescent light emitting material of claim 4, wherein the beta-diketonate includes benzoyl acetone.

22. The phosphorescent light emitting material of claim 4, wherein the beta-diketonate includes thenoyl trifluoroacetone.

23. The phosphorescent light emitting material of claim 4, wherein the beta-diketonate includes 1,3-di(2-furyl)-1,3-propanedione.

24. The phosphorescent light emitting material of claim 4, wherein the beta-diketonate includes nathphoyl trifluoroacetone.

25. The phosphorescent light emitting material of claim 14, wherein the sulfoxide ligand is selected from the group consisting of dimethyl sulfoxide (DMSO), diethyl sulfoxide (DESO), dipropyl sulfoxide (DPrSO), dibutyl sulfoxide (DBuSO), dipentyl sulfoxide (DPeSO), dihexyl sulfoxide (DHSO), diphenylsulfoxide (DPSO), methyl ethyl sulfoxide (MPSO), methyl propyl sulfoxide (MPrSO), (methyl butyl sulfoxide (MBSO), ethyl propyl sulfoxide (EPrSO), ethyl butyl sulfoxide (EBSO), propyl butyl sulfoxide (PrBSO), methyl phenyl sulfoxide (MPSO), ethyl phenyl sulfoxide (EPSO), propyl phenyl sulfoxide (PrPSO), butyl phenyl sulfoxide (BPSO), methyl tolyl sulfoxide (MTSO), ethyl tolyl sulfoxide (ETSO), propyl tolyl sulfoxide (PrTSO), butyl tolyl sulfoxide (BTSO), methyl xylyl sulfoxide (MXSO), ethyl xylyl sulfoxide (EXSO) propyl xylyl sulfoxide (PrXSO) and butyl xylyl sulfoxide (BXSO).

26. A phosphorescent light emitting material, the material is a complex compound comprises a beta-diketonate ligand, a sulfoxide ligand and a triple charge rare earth metal ion, the phosphorescent light emitting material has a following structure

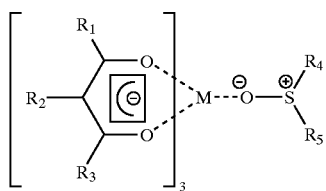

wherein M is a triple charge rare earth group metal ion, $R_2$ is hydrogen, $R_1$ and $R_3$ are selected from the group consisting of hydrogen, $C_1$ to $C_8$ straight chain alkyl groups, $C_3$ to $C_8$ branch chain alkyl groups, heterocyclic groups and $C_6$ to $C_{14}$ aryl groups, and $R_4$ and $R_5$ are selected from the group consisting of a substituted alkyl group, an unsubstituted alkyl group, an aryl group and a heterocyclic group;

wherein the phosphorescent light emitting material is used for forming a thin film of an electroluminescent device.

27. The phosphorescent light emitting material of claim 26, wherein the triple charge rare earth metal ion is selected from the group consisting of Tb(III), Eu(III), Dy(III) and Gd(III).

28. The phosphorescent light emitting material of claim 26, wherein the beta-diketonate is a tri(2,2,6,6-tetramethyl-3,5-heptanedione).

29. The phosphorescent light emitting material of claim 26, wherein the sulfoxide ligand comprises dimethyl sulfoxide.

30. The phosphorescent light emitting material of claim 26, wherein the sulfoxide ligand comprises diphenyl sulfoxide.

31. The phosphorescent light emitting material of claim 26, the sulfoxide ligand comprises methyl phenyl sulfoxide.

32. A electroluminescent device, comprising:
a thin film, wherein the thin film comprises:
a phosphorescent light emitting material with an abbreviated chemical formula of $M(L1)_3L2$, wherein
M is a triple charge rare earth group metal ion;
L1 is a diketonate ligand; and
L2 is a sulfoxide ligand.

33. An electroluminescent device, comprising:
a thin film, wherein the thin film comprises:
a phosphorescent light emitting material, the material is a complex compound comprises

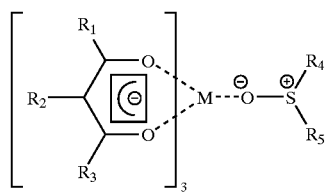

a beta-diketonate ligand, a sulfoxide ligand and a triple charge rare earth metal ion, the phosphorescent light emitting material has a following structure wherein M is a triple charge rare earth group metal ion, $R_2$ is hydrogen, $R_1$ and $R_3$ are selected from the group consisting of hydrogen, $C_1$ to $C_8$ straight chain alkyl groups, $C_3$ to $C_8$ branch chain alkyl groups, heterocyclic groups and $C_6$ to $C_{14}$ aryl groups, and $R_4$ and $R_5$ are selected from the group consisting of a substituted alkyl group, an unsubstituted alkyl group, an aryl group and a heterocyclic group.

* * * * *